United States Patent
Zhang et al.

(10) Patent No.: US 8,269,047 B2
(45) Date of Patent: Sep. 18, 2012

(54) SYNTHESIS OF ALPHA-HALO ENONES AND ENALS

(75) Inventors: Liming Zhang, Goleta, CA (US); Longwu Ye, Goleta, CA (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 159 days.

(21) Appl. No.: 12/830,957

(22) Filed: Jul. 6, 2010

(65) Prior Publication Data

US 2011/0021806 A1 Jan. 27, 2011

Related U.S. Application Data

(60) Provisional application No. 61/227,866, filed on Jul. 23, 2009.

(51) Int. Cl.
*C07C 45/30* (2006.01)
*C07C 67/327* (2006.01)

(52) U.S. Cl. ......... 568/322; 568/376; 568/404; 568/488

(58) Field of Classification Search .................. 568/322, 568/376, 404, 488
See application file for complete search history.

(56) References Cited

OTHER PUBLICATIONS

Yu, Meng, Li, Guotao, Wang, Shaozhong and Zhang, Liming, Gold-Catalyzed Efficient Formation of [alpha][beta]-Unsaturated Ketones from Propargylic Acetates, Adv. Synth. Catal. 2007, pp. 871-875, 349.
Yu, Meng, Zhang, Guozhu and Zhang, Liming, Gold-Catalyzed Efficient Preparation of Linear [alpha]-Iodoenones from Propargylic Acetates, Org. Lett. 2007, pp. 2147-2150, vol. 9, No. 11.
Zhao, Jing, Hughes, Colin O. and Toste, F. Dean, Synthesis of Aromatic Ketones by a Transition Metal-Catalyzed Tandem Sequence, J. Am. Chem. Soc. 2006, pp. 7436-7437, 128.
Egi, Masahiro, Yamaguchi, Yoshiko, Fujiwara, Noboru and Akai, Shuji, Mo-Au combo Catalysis for Rapid 1,3-Rearrangement of Propargyl Alcohols into [alpha][beta]-Unsaturated Carbonyl Compounds, Org. Lett. 2008, pp. 1867-1870, vol. 10, No. 9.
Yu, Meng, Zhang, Guozhu and Zhang, Liming, Gold-Catalyzed Efficient Preparation of Linear [alpha]-Haloenones From Propargylic Acetates, Tetrahedron 2009, pp. 1846-1855, 65.
Ramon, Ruben S., Marion, Nicolas and Nolan, Steven P., [(NHC)AuCl]-catalyzed Meyer-Schuster Rearrangement: Scope and Limitations, Tetrahedron 2009, pp. 1767-1773, 65.
Zhang, Liming, Tandem Au-Catalyzed 3,3-Rearrangement-[2+2] Cycloadditions of Propargylic Esters: Expeditious Access to Highly Functionalized 2,3-Indoline-Fused Cyclobutanes, J. Am. chem. Soc. 2005, pp. 16804-16805, 127.
Mezailles, Nicolas, Ricard, Louis and Gagosz, Fabien, Phosphine Gold(I) Bis-(trifluoromethanesulfonyl)imidate Complexes as New Highly Efficient and Air-Stable Catalysts for the Cycloisomerization of Enynes, Org. Lett. 2005, pp. 4133-4136, vol. 7, No. 19.
Engel, Douglas A. and Dudley, Gregory B., Olefination of Ketones Using a Gold (III)-Catalyzed Meyer-Schuster Rearrangement, Org. Lett. 2006, pp. 4027-4029, vol. 8, No. 18.
Shibahara, Setsyua, Fujino, Masataka, Tashiro, Yasumasa, Takahashi, Keisuke, Ishihara, Jun and Hatakeyama, Susumi, Asymmetric Total Synthesis of (+)-Phoslactomycin B, Org. Lett. 2008, pp. 2139-2142, vol. 10, No. 11.
Chen, Shufeng and Jianbo, Wang, One-Pot Synthesis of [alpha]-Iodo-Substituted [alpha][beta]-Unsaturated Aldehydes from Propargylic Alcohols, J. Org. Chem 2007, pp. 4993-4996, 72.
Antonioletti, R., D'Auria, M., Piancatelli, G, Scettri, A., Pyridinium Dichromate in Organic Synthesis: A Convenient Oxidation of [alpha]-Ynol-Iodine Complexes to [alpha][beta]-Unsaturated-[alpha]Iodo-Aldehydes, Tetrahedron Letters 1981, pp. 1041-1042, vol. 22.
Zhang, Liming and Wang, Shaozhong, Efficient Synthesis of Cyclopentenones from Enynyl Acetates via Tandem Au (I)-Catalyzed, 3,3-Rearrangement and the Nazarov Reaction, J. Am. Chem. Soc. 2006, pp. 1442-1443, 128.

*Primary Examiner* — Sikarl Witherspoon
(74) *Attorney, Agent, or Firm* — Wood, Herron & Evans, LLP

(57) ABSTRACT

A method for preparing an α-halo enal or enone from an unprotected propargyl alcohol and an electrophilic halogen source catalyzed by the combination of a gold catalyst complex and a metal co-catalyst complex is disclosed. The method can be further enhanced by addition of an additive that facilitates suppression of a des-halo derivative.

20 Claims, No Drawings

SYNTHESIS OF ALPHA-HALO ENONES AND ENALS

CROSS-REFERENCE TO RELATED APPLICATIONS

This application claims the benefit of U.S. Provisional Application No. 61/227,866, filed Jul. 23, 2009, which is hereby incorporated by reference herein in its entirety.

GOVERNMENT FUNDING

This invention was made with support under Grant Number CHE-0748484, awarded by the National Science Foundation; the United States federal government, therefore, has certain rights in the invention.

FIELD OF THE INVENTION

The present invention is directed to a catalytic synthesis of α-halo-α,β-unsaturated aldehydes/ketones directly from propargyl alcohols. This reaction is catalyzed by gold and a metal co-catalyst and, for example, foregoes the need to use an acyl group on the hydroxyl group of the propargyl alcohol.

BACKGROUND OF THE INVENTION

α-halo-α,β-unsaturated aldehydes/ketones, which are also known in the art as α-halo enals/enones, are versatile intermediates in the field of organic synthesis. While these compounds are very attractive to synthetic chemists, synthesizing these substrates has proven to be challenging and lacking in overall efficiency.

Prior methods to produce α-iodo enals, for example, have shown to be deficient because they may require multiple steps, require strong conditions, or may be limited in substrate scope. By way of example, an α-iodo enal may be synthesized from propanediol over a lengthy five-step sequence: (1) a mono-protection of the diol, (2) an oxidation of the free hydroxyl group to the aldedyhe, (3) a Horner-Emmons reaction using in situ-generated triethyl iodophosphonoacetate, (4) a reduction of the ester to the alcohol, and (5) an oxidation of the alcohol to the aldehyde. See Shibahara, S.; Fujino, M.; Tashiro, Y.; Takahashi, K.; Ishihara, J.; Hatakeyama, S. *Org. Lett.* 2008, 10, 2139-2142. In another example, treating a propargyl alcohol derivative with aqueous hydroiodic acid in toluene provides an iodoallene intermediate, which can be oxidized with molecular oxygen to yield the α-iodo enal. See Chen, S.; Wang, J. *J. Org. Chem.* 2007, 72, 4993-4996. In yet another example, propargyl alcohol derivatives may be treated with iodine, followed by oxidation with over two equivalents of pyridinium dichromate to provide the α-iodo enal. See Antonioletti, R.; D'Auria, M.; Piancatelli, G.; Scettri, A. *Tetrahedron Lett,* 1981, 22, 1041-2.

Recently, it has been shown that α-halo-α,β-unsaturated aldehydes and ketones may be prepared from propargyl acetates under catalytic conditions. While catalytic reactions are generally considered efficient, this methodology requires a propargyl ester precursor, i.e., an acetate group on the propargyl hydroxyl group, and is understood to be limited in scope. See Yu, M.; Zhang, G.; Zhang, L. *Org. Lett.* 2007, 9, 2147-2150. Accordingly, there is still a need in the art for a simple and efficient, catalytic method of synthesizing a broad variety of α-halo-α,β-unsaturated aldehydes and ketones.

SUMMARY OF THE INVENTION

In accordance with an embodiment of the invention, a method for making an α-halo enone or enal is disclosed, which includes reacting a propargyl alcohol with an electrophilic halogen source in the presence of a gold catalyst complex and a metal co-cataylst complex to form the α-halo enone or α-halo enal.

In another embodiment, the catalytic method for producing an α-halo enone or enal includes mixing a propargyl alcohol, an electrophilic halogen source, a gold catalyst complex, a metal co-catalyst complex, and a solvent. Then, the mixture is maintained under suitable reaction conditions to convert the propargyl alcohol to the α-halo enone or enal.

DETAILED DESCRIPTION OF THE INVENTION

The present invention provides improved methods for metal-catalyzed conversion of propargyl alcohols to α-halo-α,β-unsaturated aldehydes or ketones, also referred to as α-halo enals or enones, respectively, without a need, for example, for an acyl group, such as a carboxyl group, on the hydroxyl group of the propargyl alcohol.

The following terms are defined for use herein:

Alkyl group refers to saturated hydrocarbon groups, which may be linear, branched, or cyclic. Small alkyl groups are those having from one to six carbon atoms. Alkyl groups may be substituted so long as the substituents do not significantly detrimentally affect the function of the compound or portion of the compound in which it is found.

Aryl group refers to groups which contain at least one aromatic ring, which can be a five-member or a six-member ring. The one or more rings of an aryl group can include fused rings. Aryl groups may be substituted with one or more alkyl groups, which may be linear, branched or cyclic. Aryl groups may also be substituted at ring positions with substituents that do not significantly detrimentally affect the function of the compound or portion of the compound in which it is found. Substituted aryl groups also include those having heterocyclic aromatic rings in which one or more heteroatoms (e.g., N, O, or S, optionally with hydrogen or a substituent for proper valence) replace one or more carbons in the ring.

"Des-halo" refers to the absence of halogen incorporation at the alpha position of the α,β-unsaturated aldehyde or ketone, i.e., the alpha position is substituted by hydrogen instead of a halogen, e.g., iodine or bromine.

"Room temperature" is defined as having a temperature of about 18° C. to about 25° C. In one example, room temperature may be 22° C.

"Anhydrous solvent" refers to the moisture content of a solvent and is generally obtained by treating the solvent with a dehydrating reagent to remove the moisture content. For example, anhydrous $CH_2Cl_2$ is obtained via distillation over $CaH_2$. As understood by those skilled in the art, anhydrous solvents may also be commercially purchased.

In accordance with embodiments of the present invention, a catalytic method for producing an α-halo enal or enone from a propargyl alcohol is shown in Scheme 1.

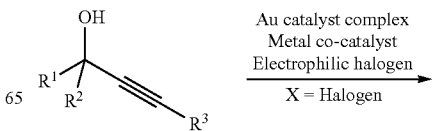

Scheme I

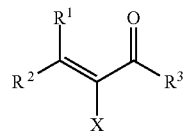

The general methodology for producing the α-halo enone or enal from a propargyl alcohol includes combining a propargyl alcohol, an electrophilic halogen source, a gold catalyst complex, and a metal co-catalyst complex, and maintaining the resulting combination under suitable reaction conditions to convert the propargyl alcohol to its corresponding α-halo enal or enone.

Concerning $R^1$ and $R^2$, these may be the same or different and can include hydrogen, substituted- or unsubstituted-alkyl, cycloalkyl, aryl, and the like, or $R^1$ and $R^2$ may be covalently bonded to form a carbocyclic or heterocyclic ring. When $R^1$ and $R^2$ are different, two geometric isomers may be produced, the Z-isomer and the E-isomer. Generally, the methodology favors the production of the Z-isomer. $R^3$ may be hydrogen, a substituted- or unsubstituted-alkyl, cycloalkyl, or aryl, and the like. X is a halogen. In one example, X is bromine or iodine.

Suitable propargyl alcohols include a variety of substitution patterns amenable to producing the subject α-halo enals or enones. For example, when $R^3$ is hydrogen, which gives an unsubstituted terminal alkyne, the starting propargyl alcohol can be converted to an α-halo enal. Conversely, when $R^3$ is a carbon moiety, such as a substituted- or unsubstituted-alkyl, cycloalkyl, aryl, and the like, the propargyl alcohol is converted to an α-halo enone.

The gold catalyst complex may be provided as a gold (I) catalyst with the general formula LAuY, wherein L is a ligand and Y is a non-coordinating anion. Exemplary ligands include phosphine, phosphite, or N-heterocyclic carbene ligands.

Phosphine ligands may be of the general formula $PR^6R^7R^8$, wherein $R^6$, $R^7$, and $R^8$ may be the same or different and may include substituted- or unsubstituted-alkyl, cycloalkyl, aryl, and the like. For example, $PPh_3$, $PEt_3$, $PBu_3$, $PCy_3$, $P(tBu)_3$, 2-(di-tert-butylphosphino)biphenyl, and 2-(dicyclohexylphosphino) biphenyl are suitable phosphine ligands. Phosphite ligands may be of the general formula of $P(OR^9)_3$, wherein $R^9$ may be substituted- or unsubstituted- alkyl, cycloalkyl, or aryl groups.

N-heterocyclic carbene (NHC) ligands are most frequently derived from the deprotonation of the corresponding azolium salts, such as imidazolium, dihydroimidazolium, triazolium, tetrazolium, pyrazolium, benzimidazolium, oxazolium, or thiazolium salts. For example, N,N'-bis(adamantyl)imidazol-2-ylidene, N,N'-bis(2,4,6-trimethylphenyl)imidazol-2-ylidene, N,N'-bis(2,6-triisopropylphenyl) imidazol-2-ylidene, N,N'-bis(isopropyl)-4,5-dimethylimidazol-2-ylidene, N,N'-bis(isopropyl) imidazol-2-ylidene, N,N'-bis (tert-butyl)imidazol-2-ylidene, N,N'-bis(2,6-diisopropylphenyl)-4,5-dihydroimidazol-2-ylidene, or N,N'-bis(2,4,6-trimethylphenyl)-4,5-dihydroimidazol-2-ylidene are suitable NHC ligands.

Non-coordinating anions (Y) include, but are not limited to, $Tf_2N^-$, $ClO_4^-$, $SbF_6^-$, $BF_4^-$, $PF_6^-$, $NO_3^-$, $TfO^-$, wherein Tf represents the trifluoromethylsulfonyl ($F_3CSO_2$) group.

Alternatively, the gold for the gold catalyst complex may be provided as a Au(III) complex, such as $AuX_3$, wherein X is a halogen. Examples of suitable Au(III) complexes are $AuI_3$, $AuBr_3$, $NaAuCl_4$, $KAuCl_4$, dichloro(nicotinic acid) Au(III) complex or the like.

In other embodiments, the gold (I) catalyst complex may be prepared during or prior to forming the reaction mixture. The gold catalyst complex may be prepared in situ by combining a suitable gold catalyst precursor with a separate ligand or non-coordinating anion source in a suitable solvent. For example, $(Ph_3P)AuCl$ and $AgNTf_2$ will undergo a metathesis reaction to provide a gold catalyst complex $(Ph_3P)AuNTf_2$, along with AgCl as a by-product.

The amount of gold catalyst complex may range from about 0.1 to about 20 mole percent based on the propargyl alcohol. In one embodiment, the gold catalyst complex is present in about 1 to about 5 mole percent. In another embodiment, the gold catalyst complex is present in about 2 mole percent.

According to various embodiments, the metal co-catalyst complex may comprise a variety of different metals, such as vanadium (V), rhenium (Re), tungsten (W), or molybdenum (Mo). Suitable non-limiting examples of the metal co-catalyst complex include $VO(acac)_2$, wherein acac is the acetylacetonate anion ligand, $CH_3ReO_3$, $ReO_3(OSiR^{10}_3)$ wherein $R^{10}$ may be a substituted- or unsubstituted-alkyl, cycloalkyl, or aryl group, $WO_3$, and those complexes having the general formula $MoO_2(L')_2$, wherein L' is a bidentate ligand such as the acetylacetonato (acac) ligand. In one example, one suitable source of molybdenum is $MoO_2(acac)_2$. Other exemplary molybdenum sources include those of the general formulas I, II, or III:

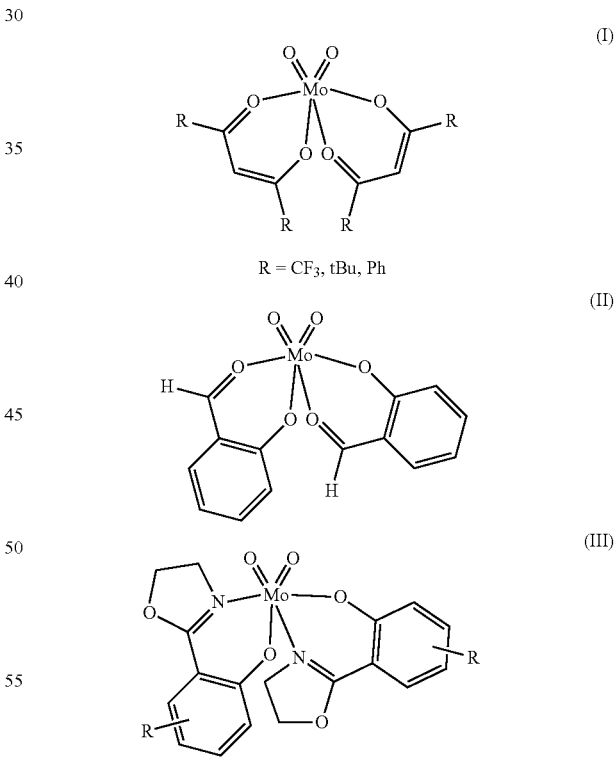

The amount of metal co-catalyst can range from about 0.1 to about 20 percent based on the moles of the propargyl alcohol. In one embodiment, the metal co-catalyst is present in about 1 to about 5 mole percent. In another embodiment, the metal co-catalyst is present in about 2 mole percent.

An additive can be included in the reaction mixture to inhibit or suppress the competitive formation of the des-halo enone or enal. Exemplary additives include sulfoxides, such as dimethylsulfoxide (DMSO), phosphine oxides, such as triphenylphosphine oxide ($Ph_3PO$) and tributylphosphine oxide ($nBu_3PO$), phosphoramides, such as hexamethylphosphoramide (HMPA), amides, such as dimethylformamide (DMF) or N-methylpyrollidinone (NMP), urethanes, ureas, and water ($H_2O$). The additive may be added to the reaction mixture in an amount up to about 40 mole percent, based on the propargyl alcohol. In one example, the additive can be present in about 5 to about 15 mole percent.

In another embodiment, the amount of additive is determined relative to the amount of metal co-catalyst. For example, the ratio of moles of the metal to moles of additive may be from about 1:1 to about 1:10.

The electrophilic halogen source can include halo-succinamides, such as N-bromosuccinamide (NBS) or N-iodosuccinamide (NIS), halo-saccharins, such as N-bromosaccharin or N-iodosaccharin, trihaloisocyanuric acids, such as tribromo- or triiodo-cyanuric acid, and the like. Other electrophilic halogen sources include bromine, mixed halogens, such as I—Br, and Br—Cl, hypervalent iodine moieties, such as bis(pyridine)iodonium tetrafluoroborate, and iodine ($I_2$) in combination with an oxidant. Exemplary oxidants include $HIO_3$, $HNO_3$, $SO_3$, $CH_3CO_3H$, $H_2O_2$, $tBuOOH$, $CuI$, $CuCl_2$, $CuBr_2$ or $Al_2O_3$, $PhI(O_2CCH_3)_2$, and $PhI(O_2CCF_3)_2$.

The equivalents of electrophilic halogen used in the reaction may range from about 1 to about 3, based on the equivalents of propargyl alcohol. In one embodiment, about 1.2 equivalents of NBS or NIS is suitable to facilitate mostly complete conversion of the starting propargyl alcohol to the desired α-halo enal or enone.

The reaction is typically carried out in an anhydrous solvent medium. Suitable solvents include non-coordinating or weakly coordinating solvents. For example, halogenated alkane solvents, such as dichloromethane (DCM) or dichloroethane (DCE) are amenable to the method described herein. A suitable quantity of solvent is used to obtain a concentration of about 0.001 moles per liter to about 2 moles per liter, based on the propargyl alcohol. For example, the concentration may be about 0.05 moles per liter.

The reaction may be performed over a wide temperature range from about 0° C. to about 60° C. In one example, the reaction mixture may be maintained at a temperature of about 15° C. to about 45° C. In another example, the reaction is performed at room temperature. In yet another example, the reaction mixture is first cooled to about 0° C. and subsequently warmed to room temperature or above.

While not specifically required, the reaction may be performed under an inert atmosphere. For example, inert gases, such as nitrogen or argon, may be used to purge the reaction vessel prior to charging reagents. Alternatively, the reaction vessel can be maintained under a positive pressure of inert gas over the course of the reaction.

Reaction times may vary depending on a variety of factors, such as reaction temperature, reaction concentration, solvent, catalyst, additive, electrophilic halogenating moiety, and the like. For example, the reaction time may be from about 1 hour to about 24 hours at room temperature. In one example, the reaction time may be from about 3 to about 11 hours.

The present invention is illustrated by the following examples that are merely for the purpose of illustration and are not to be regarded as limiting the scope of the invention or the manner in which it can be practiced.

General Reagents and Analytical Methods

Ethyl acetate (ACS grade), hexanes (ACS grade) and diethyl ether (ACS grade) were purchased from Fisher Scientific and used without further purification. Anhydrous dichloromethane in Pure-Pac™ from Aldrich was used directly without further purification. N-Iodosuccinimide was purchased from Alfa Aesar. N-Bromosuccinimide was purchased from Acros Organics. Commercially available reagents were used without further purification. Reactions were monitored by thin layer chromatography (TLC) using silicycle precoated silica gel plates. Flash column chromatography was performed over silicycle silica gel (230-400 mesh). 1H NMR and 13C NMR spectra were recorded on a Varian 400 MHz spectrometer using residue solvent peaks as internal standards. Infrared spectra were recorded with a Perkin Elmer FT-IR spectrum 2000 spectrometer and are reported in reciprocal centimeter (cm-1). Mass spectra were recorded with Waters micromass ZQ detector using electron spray method.

General Procedure for Additive Screening

An additive (0.003 mmol or 0.015 mmol), $MoO_2(acac)_2$ (1.0 mg, 0.003 mmol), $Au(PPh_3)NTf_2$ (2.2 mg, 0.003 mmol), and NIS (81 mg, 0.36 mmol) were added sequentially to a solution of the propargyl alcohol 2 (0.30 mmol), identified in Table 1 below, in anhydrous $CH_2Cl_2$ (6.0 mL, 0.05 M) at room temperature. The reaction was stirred for three hours before quenched with saturated aqueous sodium bisulfite. The mixture was extracted with diethyl ether ($Et_2O$) (3×8 mL). The combined organic phases were washed with $H_2O$ (10 mL) and brine (10 mL), dried with anhydrous $MgSO_4$, and filtered. The filtrate was concentrated, and the residue was analyzed to determine the yield of the desired α-iodo-α,β-unsaturated carbonyl compound 3, the Z/E isomeric ratio, and to quantify the amount of the des-halo derivative 4. The results are shown in Table 1.

Compound 3 was prepared as a mixture of geometrical isomers (Z/E=16/1) in 98% yield. 1H NMR (400 MHz, $CDCl_3$) (major isomer) δ 6.97 (t, 1H, J=6.8 Hz), 2.80 (t, 2H, J=7.2 Hz), 2.39 (q, 2H, J=7.2 Hz), 1.64-1.51 (m, 4H), 1.37-1.28 (m, 6H), 0.92-0.87 (m, 6H); 13C NMR (100 MHz, $CDCl_3$) δ 194.9, 151.8, 112.4, 37.9, 37.5, 31.4, 27.3, 27.1, 22.4, 22.2, 13.9, 13.8; IR (neat): 2958, 2930, 2872, 1686, 1605, 1457, 1379, 1262, 1163, 1124, 1090, 874; MS ($ES^+$) Calculated for $[C_{12}H_{21}INaO]^+$: 331.1. Found: 330.9.

TABLE 1

Bimetallic Au/Mo Catalysis with Additive

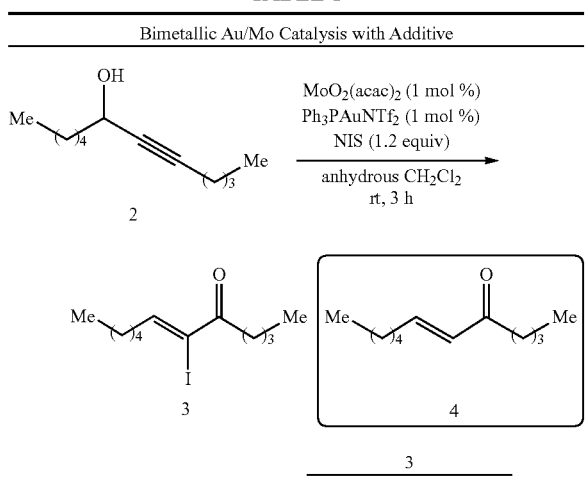

| entry[a] | additive | yield (%)[b] | Z/E[c] | 4 (%) |
|---|---|---|---|---|
| 1 | — | 54 | 6/1 | 36 |
| 2 | DMSO (5 mol %) | 72 | 24/1 | 12 |
| 3 | DMF (5 mol %) | 69 | 11/1 | 28 |
| 4 | HMPA (5 mol %) | 80 | 26/1 | <2 |
| 5 | $Ph_3PO$ (5 mol %) | >98[d] | 16/1 | <2 |
| 6 | $Ph_3PO$ (1 mol %) | 71 | 12:1 | 9 |

TABLE 1-continued

| 7 | Ph$_3$PO (5 mol %), no Au | 13[e] | 30/1 | <1 |
| 8 | No Au | 3[e] | — | — |
| 9 | Ph$_3$PO (5 mol %), no Mo | 7[e] | — | <1 |
| 10 | no Mo | 7[e] | — | <1 |

[a]Reaction concentration was 0.05 M.
[b]Estimated by $^1$H NMR using diethyl phthalate as internal reference.
[c]The geometries of 3 were determined by NOESY1D experiments.
[d]98% isolated yield.
[e]The rest of the starting material remained unreacted.

General Procedure for the Preparation of α-Iodo Enal or Enone

Ph$_3$PO (4.2 mg, 0.015 mmol), MoO$_2$(acac)$_2$ (1.0 mg, 0.003 mmol), Au(PPh$_3$)NTf$_2$ (2.2 mg, 0.003 mmol), and NIS (81 mg, 0.36 mmol) were added sequentially to a solution of the propargyl alcohol 5 (0.30 mmol), identified in Table 2 below, in anhydrous CH$_2$Cl$_2$ (6.0 mL, 0.05 M) at room temperature. The reaction was stirred for three hours before quenched with saturated aqueous sodium bisulfite. The mixture was extracted with diethyl ether (Et$_2$O) (3×8 mL). The combined organic phases were washed with H$_2$O (10 mL) and brine (10 mL), dried with anhydrous MgSO$_4$, and filtered. The filtrate was concentrated, and the residue was purified through silica gel flash column chromatography (hexanes/ethyl acetate=50/1) to yield the desired α-iodo-α,β-unsaturated carbonyl compound 6, which are identified and characterized in Table 2 below.

Compound 6a was isolated as a mixture of geometrical isomers (Z/E=36/1) in 90% yield. Its NMR spectra was identical to those previously reported. 1H NMR (400 MHz, CDCl$_3$) (major isomer) δ 7.12 (q, 1H, J=6.8 Hz), 2.82 (t, 2H, J=7.6 Hz), 2.08 (d, 3H, J=6.8 Hz), 1.63 (Quintet, 2H, J=7.6 Hz), 1.34 (Sextet, 2H, J=7.6 Hz), 0.92 (t, 3H, J=7.6 Hz). 13C NMR (100 MHz, CDCl$_3$) (major isomer) δ 194.9, 146.8, 114.3, 37.5, 30.3, 27.1, 23.9, 22.3, 13.8.

Compound 6b was prepared as a mixture of geometrical isomers (Z/E=17/1) in 93% yield. 1H NMR (400 MHz, CDCl$_3$) (major isomer) δ 6.73 (d, 1H, J=8.8 Hz), 2.84-2.79 (m, 3H), 1.62 (Quintet, 2H, J=7.6 Hz), 1.36 (Sextet, 2H, J=7.6 Hz), 1.12 (d, 6H, J=9.2 Hz), 0.92 (t, 3H, J=7.2 Hz); 13C NMR (100 MHz, CDCl$_3$) δ 195.2, 157.1, 109.7, 37.5, 37.4, 27.1, 22.2, 20.8, 13.8; IR (neat): 2962, 2930, 2872, 1686, 1604, 1466, 1268, 1166, 1128, 1088, 874; MS (ES$^+$) Calculated for [C$_{10}$H$_{17}$INaO]$^+$: 303.0. Found: 303.0.

Compound 6c was prepared as a mixture of geometrical isomers (Z/E=10/1) in 81% yield. Its NMR spectra was identical to those previously reported. 1H NMR (400 MHz, CDCl$_3$) (major isomer) δ 7.08 (q, 1H, J=7.0 Hz), 3.20-3.10 (m, 1H), 2.08 (d, 3H, J=7.0 Hz), 1.81-1.78 (m, 4H), 1.48-1.21 (m, 6H). 13C NMR (100 MHz, CDCl$_3$) δ 198.2, 146.1, 113.9, 45.4, 29.9, 25.8, 25.7, 24.0.

Compound 6d was prepared in 82% yield in a 6:1 Z/E ratio of separable isomers. The NMR spectra was identical to those previously reported. Compound Z-6d: 1H NMR (400 MHz, CDCl$_3$) δ 7.69 (d, 2H, J=8.4 Hz), 7.55 (t, 2H, J=8.0 Hz), 7.44 (t, 2H, J=7.6 Hz), 6.74 (q, 1H, J=8.0 Hz), 2.09 (d, 3H, J=8 Hz). 13C NMR (100 MHz, CDCl$_3$) δ 191.9, 149.7, 135.8, 132.4, 129.6, 128.4, 110.5, 23.6.

Compound 6e was prepared in 83% yield in a 6:1 Z/E ratio of separable isomers. Compound Z-6e: 1H NMR (400 MHz, CDCl$_3$) δ 8.02 (s, 1H), 7.79-7.76 (m, 2H), 7.46-7.43 (m, 3H), 2.98 (t, 2H, J=7.6 Hz), 1.71 (Quintet, 2H, J=7.6 Hz), 1.40 (Sextet, 2H, J=7.6 Hz), 0.96 (t, 3H, J=7.6 Hz); 13C NMR (100 MHz, CDCl$_3$) δ 196.1, 146.4, 135.7, 130.1, 129.6, 128.3, 107.6, 38.0, 27.2, 22.3, 13.9; IR (neat): 3343, 2958, 2930, 2872, 1681, 1594, 1573, 1493, 1446, 1340, 1265, 1148, 1096, 1073, 924, 873, 753; MS (ES$^+$) Calculated for [C13H15INaO]$^+$: 337.0. Found: 336.9. Compound E-6e: 1H NMR (400 MHz, CDCl$_3$) δ 7.42 (s, 1H), 7.34-7.31 (m, 3H), 7.20-7.17 (m, 2H), 2.50 (t, 2H, J=7.6 Hz), 1.54 (Quintet, 2H, J=7.6 Hz), 1.22 (Sextet, 2H, J=7.6 Hz), 0.81 (t, 3H, J=7.6 Hz); 13C NMR (100 MHz, CDCl$_3$) δ 203.6, 142.8, 136.4, 129.0, 128.7, 128.0, 97.3, 40.1, 26.2, 22.0, 13.7; IR (neat): 3059, 3026, 2960, 2930, 2872, 1698, 1599, 1573, 1495, 1465, 1447, 1402, 1261, 1127, 1073, 925, 800, 758, 696; MS (ES$^+$) Calculated for [C$_{13}$H$_{15}$INaO]$^+$: 337.0. Found: 337.1.

Compound 6f was prepared as a mixture of geometrical isomers (Z/E=30/1) in 52% yield. 1H NMR (400 MHz, CDCl$_3$)) (major isomer) δ 7.31-7.18 (m, 6H), 4.16 (m, 2H), 2.06 (d, 3H, J=6.4 Hz); 13C NMR (100 MHz, CDCl$_3$) δ 192.2, 148.5, 134.3, 129.2, 128.7, 127.0, 113.2, 44.3, 24.1; IR (neat): 3064, 2920, 2851, 2211, 1675, 1607, 1496, 1454, 1371, 1291, 1230, 1160, 1083, 1031, 751, 704; MS (ES$^+$) Calculated for [C$_{11}$H$_{11}$INaO]$^+$: 309.0. Found: 308.9.

Compound 6g was prepared as a mixture of geometrical isomers (Z/E=34/1) in 87% yield with exceptions that 2 mol % Au(PPh$_3$)NTf$_2$, 2 mol % of MoO$_2$(acac)$_2$, and 10 mol % of Ph$_3$PO were used. 1H NMR (400 MHz, CDCl$_3$) (major isomer) δ 7.36-7.30 (m, 5H), 7.19 (q, 1H, J=6.4 Hz), 4.60 (s, 2H), 4.58 (s, 2H), 2.04 (d, 3H, J=6.4 Hz); 13C NMR (100 MHz, CDCl$_3$) δ 191.1, 148.6, 137.0, 128.5, 128.0, 109.4, 73.3, 71.8, 23.8; IR (neat): 3031, 2919, 2865, 1697, 1610, 1497, 1454, 1370, 1297, 1271, 1183, 1122, 1079, 1029, 806, 741; MS (ES$^+$) Calculated for [C$_{12}$H$_{13}$INaO$_2$]$^+$: 339.0. Found: 338.9.

Compound 6h was prepared as a mixture of geometrical isomers (Z/E=11/1) in 88% yield with exceptions that 2 mol % Au(PPh$_3$)NTf$_2$, 2 mol % of MoO$_2$(acac)$_2$, and 10 mol % of Ph$_3$PO were used. 1H NMR (400 MHz, CDCl$_3$) (major isomer) δ 7.12 (q, 1H, J=6.8 Hz), 3.66 (t, 2H, J=6.4 Hz), 3.29 (s, 3H), 3.03 (t, 2H, J=6.4 Hz), 2.04 (d, 3H, J=6.4 Hz); 13C NMR (100 MHz, CDCl$_3$) (major isomer) δ 192.6, 148.0, 113.9, 68.1, 58.8, 37.7, 23.9; IR (neat): 3339, 2981, 2923, 2894, 2829, 1680, 1609, 1451, 1388, 1291, 1230, 1170, 1118, 1055, 995, 966, 852, 816; MS (ES$^+$) Calculated for [C$_7$H$_{11}$NaIO$_2$]$^+$: 277.0. Found: 277.1.

Compound 6i was prepared as a mixture of geometrical isomers (Z/E>50/1) in 73% yield with exceptions that 2 mol % Au(PPh$_3$)NTf$_2$, 2 mol % of MoO$_2$(acac)$_2$, and 10 mol % of Ph$_3$PO were used. 1H NMR (400 MHz, CDCl$_3$) (major isomer) δ 8.68 (s, 1H), 7.19 (t, 1H, J=6.8 Hz), 2.55 (q, 2H, J=7.2 Hz), 1.59 (Quintet, 2H, J=7.6 Hz), 1.40-1.35 (m, 4H), 0.92 (t, 3H, J=7.2 Hz); 13C NMR (100 MHz, CDCl$_3$) δ 188.0, 162.7, 111.7, 36.5, 31.4, 27.2, 22.4, 13.9; IR (neat): 2957, 2929, 2860, 1697, 1606, 1467, 1380, 1204, 1141, 1083, 874; MS (ES$^+$) Calculated for [C$_8$H$_{13}$INaO$_2$]$^+$: 275.0. Found: 275.0.

Compound 6j was prepared in 72% yield with exceptions that 2 mol % Au(PPh$_3$)NTf$_2$, 2 mol % of MoO$_2$(acac)$_2$, and 10 mol % of Ph$_3$PO were used. 1H NMR (400 MHz, CDCl$_3$) δ 8.13 (d, 2H, J=8.8 Hz), 7.83 (d, 2H, J=8.8 Hz), 6.91 (d, 1H, J=2.4 Hz), 6.90 (d, 1H, J=2.4 Hz), 4.42 (q, 2H, J=7.2 Hz), 1.42 (t, 3H, J=7.2 Hz); 13C NMR (100 MHz, CDCl$_3$) δ 191.1, 165.5, 139.4, 137.4, 134.2, 129.5 (9), 129.5 (6), 107.9, 61.5, 14.2; IR (neat): 2982, 1718, 1671, 1587, 1501, 1407, 1368, 1278, 1177, 1106, 1021, 964, 870, 757, 741; MS (ES$^+$) Calculated for [C$_{12}$H$_{11}$NaIO$_3$]$^+$: 353.0. Found: 353.2.

Compound 6k was prepared in 78% yield with exceptions that 2 mol % Au(PPh$_3$)NTf$_2$, 2 mol % of MoO$_2$(acac)$_2$, and 10 mol % of Ph$_3$PO were used. 1H NMR (400 MHz, CDCl$_3$) δ 7.86 (d, 2H, J=8.8 Hz), 6.94 (d, 2H, J=9.2 Hz), 6.75 (d, 1H, J=2.0 Hz), 6.68 (d, 1H, J=2.4 Hz), 3.88 (s, 3H); 13C NMR (100 MHz, CDCl$_3$) δ 190.5, 163.8, 135.8, 132.5, 126.1, 113.9, 106.7, 55.5; IR (neat): 3008, 2963, 2932, 2841, 1657, 1599, 1508, 1462, 1422, 1387, 1313, 1256, 1174, 1124, 1028, 968, 845, 780; MS (ES+) Calculated for [C$_{10}$H$_9$NaIO$_2$]+: 311.0. Found: 310.8.

Compound 6l was prepared in 85% yield. 1H NMR (400 MHz, CDCl$_3$) δ 7.25 (d, 1H, J=2.8 Hz), 6.82 (d, 1H, J=2.8 Hz), 2.81 (t, 2H, J=7.6 Hz), 1.69 (Sextet, 2H, J=7.6 Hz), 0.95 (t, 3H, J=7.6 Hz); 13C NMR (100 MHz, CDCl$_3$) δ 195.0, 137.2, 113.3, 38.4, 18.1, 13.6; IR (neat): 2963, 2930, 1693, 1593, 1459, 1396, 1262, 1102, 1044; MS (ES+) Calculated for [C$_6$H$_9$NaIO]+: 247.0. Found: 247.0.

Compound 6m was prepared in 87% yield. Its NMR spectra was identical to those previously reported. 1H NMR (400 MHz, CDCl$_3$) δ 2.79 (t, 2H, J=7.2 Hz), 2.41 (t, 2H, J=6.0 Hz), 2.33 (t, 2H, J=6.0 Hz), 1.65-1.52 (m, 8H), 1.35 (Sextet, 2H, J=7.2 Hz), 0.93 (t, 3H, J=7.2 Hz). 13C NMR (100 MHz, CDCl$_3$) δ 202.5, 149.2, 92.4, 40.3, 39.6, 32.9, 28.0, 27.4, 26.3, 25.9, 22.3, 13.8.

Compound 6n was prepared in 96% yield. Its NMR spectra were identical to those previously reported. 1H NMR (400 MHz, CDCl$_3$) δ 2.81 (t, 2H, J=7.2 Hz), 2.03 (s, 3H), 1.96 (s, 3H), 1.61 (Quintet, 2H, J=7.2 Hz), 1.35 (Sextet, 2H, J=7.2 Hz), 0.93 (t, 3H, J=7.2 Hz). 13C NMR (100 MHz, CDCl$_3$) δ 202.3, 144.3, 95.5, 40.5, 30.3, 26.4, 22.3, 21.9, 13.8.

TABLE 2

Formation of α-iodoenones/enals

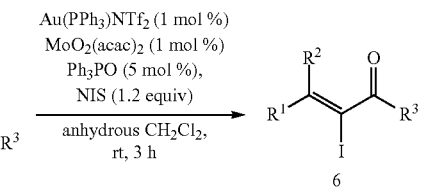

| entry[a] | propargyl alcohol | 5 | α-iodoenone | 6 | Z/E | yield [%][b,c] |
|---|---|---|---|---|---|---|
| 1 | Me-CH(OH)-C≡C-(CH$_2$)$_3$-Me | 5a | Me-CH=C(I)-C(O)-(CH$_2$)$_3$-Me | 6a | 36:1 | 90 (<2) |
| 2 | Me$_2$CH-CH(OH)-C≡C-(CH$_2$)$_3$-Me | 5b | Me$_2$CH-CH=C(I)-C(O)-(CH$_2$)$_3$-Me | 6b | 17:1 | 93 (3) |
| 3 | Me-CH(OH)-C≡C-Cy | 5c | Me-CH=C(I)-C(O)-Cy | 6c | 10:1 | 81 (<2) |
| 4 | Me-CH(OH)-C≡C-Ph | 5d | Me-CH=C(I)-C(O)-Ph | 6d | 6:1 | 82[d] (<2) |
| 5 | Ph-CH(OH)-C≡C-(CH$_2$)$_3$-Me | 5e | Ph-CH=C(I)-C(O)-(CH$_2$)$_3$-Me | 6e | 6:1 | 83 (5) |
| 6 | Me-CH(OH)-C≡C-CH$_2$-Ph | 5f | Me-CH=C(I)-C(O)-CH$_2$-Ph | 6f | 30:1 | 52 (<2) |

TABLE 2-continued

Formation of α-iodoenones/enals

[Reaction scheme: propargyl alcohol 5 (R¹, R², OH, R³) → α-iodoenone 6, with Au(PPh₃)NTf₂ (1 mol %), MoO₂(acac)₂ (1 mol %), Ph₃PO (5 mol %), NIS (1.2 equiv), anhydrous CH₂Cl₂, rt, 3 h]

| entry[a] | propargyl alcohol 5 | α-iodoenone 6 | Z/E | yield [%][b,c] |
|---|---|---|---|---|
| 7 | 5g (Me, OH, C≡C-CH₂OBn) | 6g | 34:1 | 87[e] (4) |
| 8 | 5h (Me, OH, C≡C-CH₂CH₂OMe) | 6h | 11:1 | 88[e] (6) |
| 9 | 5i (Me(CH₂)₄CH(OH)C≡CH) | 6i | >50:1 | 73[d,e] (<2) |
| 10 | 5j (HOCH₂-C≡C-C₆H₄-CO₂Et) | 6j | — | 72[e] (<2) |
| 11 | 5k (HOCH₂-C≡C-C₆H₄-OMe) | 6k | — | 78[e] (<2) |
| 12 | 5l (HOCH₂-C≡C-(CH₂)₂Me) | 6l | — | 85 (<2) |
| 13 | 5m (1-(prop-1-ynyl)cyclohexanol, Me-(CH₂)₃) | 6m | — | 87 (<2) |
| 14 | 5n (Me₂C(OH)-C≡C-(CH₂)₃Me) | 6n | — | 96 (3) |

[a]The substrate concentration was 0.05 M.
[b]Isolated yield.
[c]The yield of the corresponding enone was shown in parenthesis.
[d]Reaction time: 15 h.
[e]2 mol % Au(PPh₃)NTf₂, 2 mol % of MoO₂(acac)₂, and 10 mol % of Ph₃PO were used.

General Procedure for the Preparation of α-Bromo Enal or Enone

Ph$_3$PO (8.4 mg, 0.03 mmol), MoO$_2$(acac)$_2$ (2.0 mg, 0.006 mmol), Au(PPh$_3$)NTf$_2$ (4.4 mg, 0.006 mmol), and NBS (64 mg, 0.36 mmol) were added sequentially to a solution of the propargyl alcohol 5 (0.30 mmol), identified and in Table 3 below, in anhydrous CH$_2$Cl$_2$ (6.0 mL, 0.05 M) at room temperature. The reaction was stirred for three hours before quenched with saturated aqueous sodium bisulfite. The mixture was extracted with Et$_2$O (3×8 mL). The combined organic phases were washed with H$_2$O (10 mL) and brine (10 mL), dried with anhydrous MgSO$_4$, and filtered. The filtrate was concentrated, and the residue was purified through silica gel flash column chromatography (hexanes/ethyl acetate=50/1) to yield the desired α-bromo-α,β-unsaturated carbonyl compounds 7-10, which are identified and characterized in Table 3 below.

Compound 7 was prepared as a mixture of geometrical isomers (Z/E=20/1) in 80% yield. Its NMR spectra was identical to those previously reported. 1H NMR (400 MHz, CDCl$_3$) (major isomer) δ 7.24 (q, 1H, J=6.8 Hz), 2.77 (t, 2H, J=7.5 Hz), 2.01 (d, 3H, J=6.8 Hz), 1.62 (Quintet, 2H, J=7.6 Hz), 1.35 (Sextet, 2H, J=7.6 Hz), 0.92 (t, 3H, J=7.5 Hz). 13C NMR (100 MHz, CDCl$_3$) δ 194.3, 139.5, 128.9, 38.4, 26.7, 22.3, 18.2, 13.8.

Compound 8 was prepared as a mixture of geometrical isomers (Z/E>50/1) in 78% yield with exceptions that 5 mol % Au(PPh$_3$)NTf$_2$, 5 mol % of MoO$_2$(acac)$_2$, and 15 mol % of Ph$_3$PO were used. 1H NMR (400 MHz, CDCl$_3$) (major isomer) δ 9.21 (s, 1H), 7.15 (t, 1H, J=7.2 Hz), 2.53 (q, 2H, J=7.2 Hz), 1.57 (Quintet, 2H, J=7.2 Hz), 1.38-1.34 (m, 4H), 0.92 (t, 3H, J=7.2 Hz); 13C NMR (100 MHz, CDCl$_3$) δ 186.1, 155.9, 128.7, 32.0, 31.4, 27.2, 22.3, 13.9; IR (neat): 2959, 2931, 2861, 1703, 1618, 1458, 1380, 1272, 1208, 1147, 1089; MS (ES$^+$) Calculated for [C8H13BrNaO]$^+$: 227.0. Found: 227.0.

Compound 9 was prepared in 82% yield with exceptions that 5 mol % Au(PPh$_3$)NTf$_2$, 5 mol % of MoO$_2$(acac)$_2$, and 15 mol % of Ph$_3$PO were used. 1H NMR (400 MHz, CDCl$_3$) δ 7.86 (d, 2H, J=8.8 Hz), 6.95 (d, 2H, J=8.8 Hz), 6.41 (d, 1H, J=2.4 Hz), 6.37 (d, 1H, J=2.4 Hz), 3.88 (s, 3H); 13C NMR (100 MHz, CDCl$_3$) δ 188.9, 163.9, 132.3, 128.8, 127.9, 127.3, 113.8, 55.5; IR (neat): 3011, 2966, 2937, 2842, 1663, 1600, 1573, 1510, 1463, 1422, 1388, 1314, 1259, 1175, 1130, 1029, 967, 846, 780, 618, 585; MS (ES$^+$) Calc. for [C$_{10}$H$_9$NaBrO$_2$]$^+$: 263.0. Found: 262.8.

Compound 10 was prepared in 94% yield. Its NMR spectra was identical to those previously reported. 1H NMR (400 MHz, CDCl$_3$) δ 2.78 (t, 2H, J=7.6 Hz), 2.01 (s, 3H), 2.00 (s, 3H), 1.59 (Quintet, 2H, J=7.6 Hz), 1.35 (Sextet, 2H, J=7.6 Hz), 0.92 (t, 3H, J=7.6 Hz); 13C NMR (100 MHz, CDCl$_3$) δ 199.8, 143.3, 117.3, 41.1, 26.4, 26.3, 22.7, 22.3, 13.8. IR (neat): 2960, 2934, 2874, 1688, 1596, 1441, 1368, 1158, 1045, 920, 849; MS (ES$^+$) Calculated for [C$_9$H$_{15}$BrNaO]$^+$: 241.0. Found: 240.7.

TABLE 3

Formation of α-bromoenones/enals

| entry[a] | propargyl alcohol | 5 | α-bromoenone | | Z/E | yield [%][b,c] |
|---|---|---|---|---|---|---|
| 1 | (Me)CH(OH)C≡C(CH$_2$)$_3$Me | 5a | Me-CH=C(Br)-C(O)-(CH$_2$)$_3$Me | 7 | 20:1 | 80 (5) |
| 2 | Me(CH$_2$)$_4$CH(OH)C≡CH | 5i | Me(CH$_2$)$_4$CH=C(Br)-CHO | 8 | >50/1 | 78[d,e] (<1) |
| 3 | HO-CH$_2$-C≡C-C$_6$H$_4$-OMe | 5k | CH$_2$=C(Br)-C(O)-C$_6$H$_4$-OMe | 9 | — | 82[e] (<1) |
| 4 | Me$_2$C(OH)C≡C(CH$_2$)$_3$Me | 5n | Me(Me)C=C(Br)-C(O)-(CH$_2$)$_3$Me | 10 | — | 94 (3) |

Reagents: Au(PPh$_3$)NTf$_2$ (2 mol %), MoO$_2$(acac)$_2$ (2 mol %), Ph$_3$PO (10 mol %), NBS (1.2 equiv), anhydrous CH$_2$Cl$_2$, rt

[a]The substrate concentration was 0.05 M.
[b]Isolated yield.
[c]The yield of the corresponding enone was shown in parenthesis.
[d]Reaction time: 11 h.
[e]5 mol % Au(PPh$_3$)NTf$_2$, 5 mol % of MoO$_2$(acac)$_2$, and 15 mol % of Ph$_3$PO were used.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. A method for making an α-halo enone or enal comprising:
reacting a propargyl alcohol with an electrophilic halogen source in the presence of a gold catalyst complex and a metal co-catalyst complex to form an α-halo enone or α-halo enal.

2. The method of claim 1 wherein the α-halo enone or α-halo enal is defined by the formula:

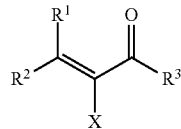

where $R^1$ and $R^2$ each independently are hydrogen, a substituted- or unsubstituted-alkyl, a cycloalkyl, or an aryl, or where $R^1$ and $R^2$ are covalently bonded to form a carbocyclic or heterocyclic ring; $R^3$ is hydrogen, a substituted- or unsubstituted-alkyl, a cycloalkyl, or an aryl; and X is a halogen.

3. The method of claim 1, wherein the propargyl alcohol is defined by the formula:

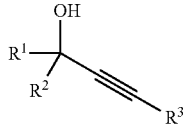

where $R^1$ and $R^2$ each independently are either hydrogen, a substituted- or unsubstituted-alkyl, a cycloalkyl, or an aryl, or where $R^1$ and $R^2$ are covalently bonded to form a carbocyclic or heterocyclic ring; and $R^3$ is hydrogen, a substituted- or unsubstituted-alkyl, a cycloalkyl, or an aryl.

4. The method of claim 2 wherein X is bromine or iodine.

5. The method of claim 3 wherein $R^3$ is hydrogen.

6. The method of claim 3 wherein $R^3$ is a substituted- or unsubstituted-alkyl, a cycloalkyl, or an aryl.

7. The method of claim 1, wherein the electrophilic halogen source is selected from a halo-succinamide, a halo-saccharin, trihaloisocyanuric acid, bromine, a mixed halogen, a hypervalent iodine moiety, or iodine in combination with an oxidant.

8. The method of claim 1, wherein the gold catalyst complex is a gold (I) catalyst having the formula LAuY, wherein Au is gold, L is a ligand, and Y is a non-coordinating anion.

9. The method of claim 1, wherein the gold catalyst complex is a Au(III) complex.

10. The method of claim 1, wherein the metal co-catalyst complex includes a metal selected from vanadium, rhenium, tungsten, or molybdenum.

11. The method of claim 1, wherein the propargyl alcohol is reacted with the electrophilic halogen source in the presence of the gold catalyst complex, the metal co-cataylst complex, a solvent, and an additive that facilitates suppression of a des-halo derivative.

12. The method of claim 11, wherein the additive is selected from a sulfoxide, a phosphine oxide, a phosphoramide, an amide, a urethane, a urea, or water.

13. The method of claim 11, wherein the solvent is an anhydrous solvent.

14. The method of claim 1 wherein the electrophilic halogen source is a halo-succinamide, the gold catalyst complex is $Au(PPh_3)NTf_2$, where Tf is $F_3(CSO_2)$, and the metal co-catalyst complex is $MoO_2(acac)_2$.

15. A method for producing an α-halo enone or enal comprising:
mixing a propargyl alcohol, an electrophilic halogen source, a gold catalyst complex, a metal co-catalyst complex, and a solvent; and
maintaining the mixture under suitable reaction conditions to convert the propargyl alcohol to a α-halo enone or enal.

16. The method of claim 15, wherein the propargyl alcohol is defined by the formula:

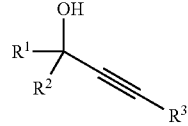

where $R^1$ and $R^2$ each independently are either hydrogen, a substituted- or unsubstituted-alkyl, a cycloalkyl, or an aryl, or where $R^1$ and $R^2$ are covalently bonded to form a carbocyclic or heterocyclic ring; and $R^3$ is hydrogen, a substituted- or unsubstituted-alkyl, a cycloalkyl, or an aryl.

17. The method of claim 16 wherein $R^3$ is hydrogen.

18. The method of claim 16 wherein $R^3$ is a substituted- or unsubstituted-alkyl, a cycloalkyl, or an aryl.

19. The method of claim 16, wherein the maintaining step comprises maintaining the mixture at a temperature from about 0° C. to about 60° C. to convert the propargyl alcohol to the α-halo enone or enal.

20. The method of claim 16, wherein the mixing step comprises mixing the propargyl alcohol, the electrophilic halogen source, the gold catalyst complex, the metal co-catalyst complex, the solvent, and an additive that facilitates suppression of a des-halo derivative.

* * * * *